(12) United States Patent
Roels et al.

(10) Patent No.: US 9,283,078 B2
(45) Date of Patent: Mar. 15, 2016

(54) PATIENT-SPECIFIC INTRALUMINAL IMPLANTS

(71) Applicant: Materialise N.V., Leuven (BE)

(72) Inventors: Toon Roels, Oud-Heverlee (BE); Peter Verschueren, Bierbeek (BE)

(73) Assignee: Materialise N.V., Leuven (BE)

( * ) Notice: Subject to any disclaimer, the term of this patent is extended or adjusted under 35 U.S.C. 154(b) by 182 days.

(21) Appl. No.: 14/032,301

(22) Filed: Sep. 20, 2013

(65) Prior Publication Data
US 2014/0088698 A1    Mar. 27, 2014

(30) Foreign Application Priority Data

Sep. 21, 2012    (EP) ..................................... 12185324

(51) Int. Cl.
*A61F 2/24* (2006.01)
*A61F 2/30* (2006.01)
*G06T 19/20* (2011.01)
*A61B 19/00* (2006.01)

(52) U.S. Cl.
CPC .......... *A61F 2/30942* (2013.01); *A61F 2/2418* (2013.01); *G06T 19/20* (2013.01); *A61B 2019/508* (2013.01); *A61F 2240/002* (2013.01); *A61F 2250/006* (2013.01); *G06T 2210/41* (2013.01); *G06T 2219/2021* (2013.01); *Y10T 29/49* (2015.01)

(58) Field of Classification Search
CPC ........... A61F 2/2418; A61F 2240/002; A61F 2/30942; A61F 2002/30945; A61F 2002/948; A61F 2002/3095; A61F 2002/30952; A61F 2002/30953; A61F 2002/30955
See application file for complete search history.

(56) References Cited

U.S. PATENT DOCUMENTS

| | | |
|---|---|---|
| 6,165,193 A | 12/2000 | Greene et al. |
| 2001/0001835 A1 | 5/2001 | Greene et al. |
| 2003/0083737 A1 | 5/2003 | Greene et al. |
| 2003/0088311 A1 | 5/2003 | Greene et al. |
| 2004/0116997 A1 | 6/2004 | Taylor et al. |
| 2007/0150052 A1 | 6/2007 | Santilli |
| 2007/0176333 A1 | 8/2007 | Greene et al. |
| 2008/0039923 A1 | 2/2008 | Taylor et al. |
| 2009/0112250 A1 | 4/2009 | Greene et al. |
| 2011/0005062 A1 | 1/2011 | Greene et al. |

OTHER PUBLICATIONS

European Search Report, dated Feb. 15, 2013 in connection with European Patent Application No. 12185324.6, 6 pages.

*Primary Examiner* — David Isabella
*Assistant Examiner* — Suba Ganesan
(74) *Attorney, Agent, or Firm* — FairView IP

(57) ABSTRACT

Methods are provided for generating intraluminal prosthetic implants designed to fit onto specific anatomical locations within regions which are stable in terms of their motion in time.

13 Claims, 6 Drawing Sheets

PATIENT-SPECIFIC INTRALUMINAL IMPLANTS

CROSS-REFERENCE TO RELATED APPLICATION

This application claims priority to European Patent Application No. 12185324.6, filed Sep. 21, 2012, the contents of which are incorporated herein by reference in their entirety.

FIELD OF THE INVENTION

Methods are provided for generating intraluminal implants which contain structural information that conforms to patient specific anatomical regions to ensure an optimal fit.

BACKGROUND

Endoprostheses are a commonly used way of dealing with diseases in interventional medicine and surgery. Mesh-based endoprostheses such as stents, stent grafts, heart valve frames, etc. are of particular importance in cardiovascular applications. Other fields of medicine also make use of such endoprostheses, e.g. pulmonary tract stents, oesophagus stents, etc.

Intraluminal endoprostheses such as stents are typically designed such that they are deployable by catheter or similar stent delivery system, as it is desirable for stent placement procedures to be minimally invasive. Some stents are self-expandable, whereas other stents are inflated via a balloon inside the stent in order to force the stent to open.

However, in some surgical cases the use of a less invasive delivery system is hindered by form, size and material of the intraluminal endoprostheses. When there are no minimally invasive endoprostheses available, a major surgical intervention is required and while this can often be conducted for the majority of the patients, the replacement of such an endoprosthesis after some years is more difficult due to the aging of the patient. Often secondary and tertiary major surgical interventions are avoided when the condition of the patient does not provide for it.

There have been some further developments in this field and docking structures have been developed onto which elements such as heart valves can be attached resulting in a fully functional endoprosthesis where the part most vulnerable to replacement (e.g. the heart valve) could be replaced using a minimal invasive surgery while the docking structure remains in place. These docking structures have also been made foldable such that these can also be introduced using minimal invasive surgical methods.

However, similar to the functional intraluminal endoprostheses, these types of structures are also prone to fixation problems as the position of the docking structure is highly unstable.

Accordingly, there is a need for improved intraluminal endoprostheses, docking structures and methods for the production of these devices.

SUMMARY OF THE INVENTION

The methods described herein are envisaged to ensure that an intraluminal implant, such as but not limited to a docking structure for a functional element, will be positioned in the optimal location in the patient's lumen. This implies positioning of the implant in an anatomical location conform to the patient's anatomy (lumen), but also in an anatomical area or zone that is stable in terms of its motion in time. To this end, the intraluminal implants are provided with an outer surface which is configured to comprise patient-specific anatomy engagement surfaces or contact points corresponding to specifically selected anatomical regions of the lumen wall. In this way, the implant can be nested stably against a specific region of the lumen wall of the patient, and has an increased chance of being maintained in this position.

In particular embodiments, methods are provided for generating a patient-specific intraluminal implants, comprising the steps of: identifying for a patient, based on information regarding the variation in function of time of the anatomy of said lumen in the anatomical area of interest for placing said intraluminal implant, the anatomical regions in said anatomical area showing greater stability in time; identifying and selecting the locations in the regions so identified which are suitable for use as a base for the contact surface of a intraluminal implant, and generating a patient-specific intraluminal implant based on this information, said implant comprising an outer surface configured to comprise one or more patient-specific anatomy engagement surfaces or contact points corresponding to locations of the anatomical regions of the lumen wall identified corresponding to both criteria.

In particular embodiments of the methods envisaged herein, the intraluminal implant is an intraluminal docking station and the methods comprise the steps of identifying for a patient, based on information regarding the variation in function of time of the anatomy of said lumen in the anatomical area of interest for placing said intraluminal docking structure, the anatomical regions in said anatomical area showing greater stability in time; identifying and selecting the locations in the regions so-identified which are suitable for use as a base for the contact surface of a intraluminal docking structure, and generating a patient-specific intraluminal docking structure based on the information obtained in the previous steps, said docking structure comprising an outer surface configured to comprise one or more patient-specific anatomy engagement surfaces or contact points corresponding to anatomical regions of the lumen wall and an inner surface comprising one or more docking features for detachably engaging said inner surface of said intraluminal docking structure with said functional element.

More particularly said step of identifying an anatomical area showing greater stability in time comprises an assessment based on parameters chosen from one or more of: 2-dimensional parameters comprising change in planar circumference, area, best fit ellipse ellipticity, best fit circle diameter and/or maximum distance across a lumen; 3-dimensional parameters comprising shortest distance around said lumen, best fit ellipsoid ellipticity, short or long axis length, best fit cylinder diameter, and/or best fit sphere diameter; and/or the degree of variation or displacement of a point or surface.

In particular embodiments, said the methods envisaged herein further comprise first step (prior to the steps described above) of obtaining from said patient information regarding the variation of the anatomy of said lumen in the anatomical area of interest for placing said intraluminal implant in function of time.

More particularly said step of identifying an anatomical area showing greater stability in time is performed based on three dimensional (3D) imaging information of the lumen anatomy of said patient. In particular embodiments step of obtaining from said patient information regarding the variation of the anatomy of said lumen comprises obtaining three dimensional (3D) imaging information of a region of the lumen anatomy of said patient over time.

Where the implant is a docking structure, the functional element for which docking structure are provided can include, but is not limited to, a valve, plug, mesh, sieve, drug eluting component.

In particular embodiments said outer surface of said intraluminal implant is configured to comprise patient-specific anatomy engagement surfaces both in regions at the distal end and at the proximal end of said lumen wall. More particularly said intraluminal implant comprises one or more attachment structures for attachment in said lumen and said patient-specific anatomy engagement surfaces correspond to external surfaces of said attachment structures.

In particular embodiments the implant or part thereof is transitionable from a collapsed state to an expanded state. More particularly said intraluminal implant or part thereof is adapted to retract radially in the collapsed state and extend radially in the expanded state. In further particular embodiments, the transitionable attachment structures are toroidal attachment structures.

In particular embodiments said intraluminal implant comprises distal and proximal transitionable attachment structures and said distal and proximal transitionable attachment structure can be independently expanded to approximately their full diameters. More particularly said intraluminal implant comprises a flexible biocompatible contractible fabric or an auxetic material or structure.

In particular embodiments, where the intraluminal implant envisaged is a docking structure, the corresponding docking features include anchoring components engaging said functional element by friction, barb, clip, staple, post, eyelet or hook.

More particularly the methods envisaged herein comprise generating said intraluminal docking structure and optionally said functional element as a single part through additive manufacturing. More particularly said intraluminal docking structure is manufactured in bio-absorbable material.

In particular embodiments said patient-specific intraluminal docking structure is a heart valve docking structure comprising a body structure which links a distal toroidal attachment structure and a proximal toroidal attachment structure; wherein said method comprises
  identifying for said patient, the anatomical regions in the anatomical area of said heart valve showing greater stability in time;
  identifying and selecting the locations in the regions identified, which are suitable for use as a base for the contact surface of a heart valve docking structure, and
  generating a patient-specific heart valve docking structure based on the information obtained in the above steps, such that said distal toroidal attachment structure comprises patient-specific anatomy engagement surfaces or contact points corresponding to said locations in anatomical regions on the outflow side of the patient's heart valve anatomy and said proximal toroidal attachment structure comprises patient-specific anatomy engagement surfaces or contact points corresponding to said locations in anatomical regions on the inflow side of the patient's heart valve anatomy.

The application further provides intraluminal implants, such as but not limited to intraluminal docking structures, and in particular heart valve docking structures, obtainable using the methods as disclosed herein.

More particularly said patient-specific intraluminal implants comprise a body structure spanning a specific patient's lumen with an outer surface configured to comprise one or more patient-specific anatomy engagement surfaces or contact points corresponding to patient-specific anatomical regions of the lumen wall, wherein said patient-specific anatomical regions of the lumen wall are pre-operatively identified anatomical regions showing greater stability in time.

In particular embodiments, the application provides intraluminal docking structures comprising
  a body structure spanning a specific patient's lumen;
  an outer surface configured to comprise one or more patient-specific anatomy engagement surfaces or contact points corresponding to patient-specific anatomical regions of the lumen wall; and;
  an inner surface comprising one or more docking features for detachably engaging said inner surface of said intraluminal docking structure with a functional element;
wherein said patient-specific anatomical regions of the lumen wall are pre-operatively identified anatomical regions showing greater stability in time.

More particularly said functional element can include, but is not limited to, a valve, plug, sieve, mesh or drug eluting component. More particularly said functional element is a standard functional element. More particularly said docking features include anchoring components engaging said functional element by friction, barb, clip, staple, post, eyelet or hook. More particularly said intraluminal docking structure and optionally said functional element are manufactured as a single part through additive manufacturing. More particularly said intraluminal docking structure is foldable. More particularly said intraluminal docking structure is manufactured in bio-absorbable material.

In particular embodiments said intraluminal docking structure is a heart valve docking structure. More particularly said heart valve docking structure comprises a body structure linking:
  a distal toroidal attachment structure and one or more patient-specific anatomy engagement surfaces or contact points corresponding to anatomical regions on the outflow side of the patient's heart valve anatomy; and
  a proximal toroidal attachment structure and one or more patient-specific anatomy engagement surfaces or contact points corresponding to anatomical regions on the inflow side of the patient's heart valve anatomy;
said body structure comprising one or more coupling features for linking a functional element to said docking structure, wherein said patient-specific engagement surfaces or contact points correspond to anatomical regions with a lower degree of variation in time compared to other anatomical regions on the inflow or outflow side of the patient's heart valve anatomy.

BRIEF DESCRIPTION OF THE DRAWINGS

The following description of the figures of specific embodiments of the invention is merely exemplary in nature and is not intended to limit the present teachings, their application or uses. Throughout the drawings, corresponding reference numerals indicate like or corresponding parts and features.

In the figures, the following numbering is used.

Figure 1:
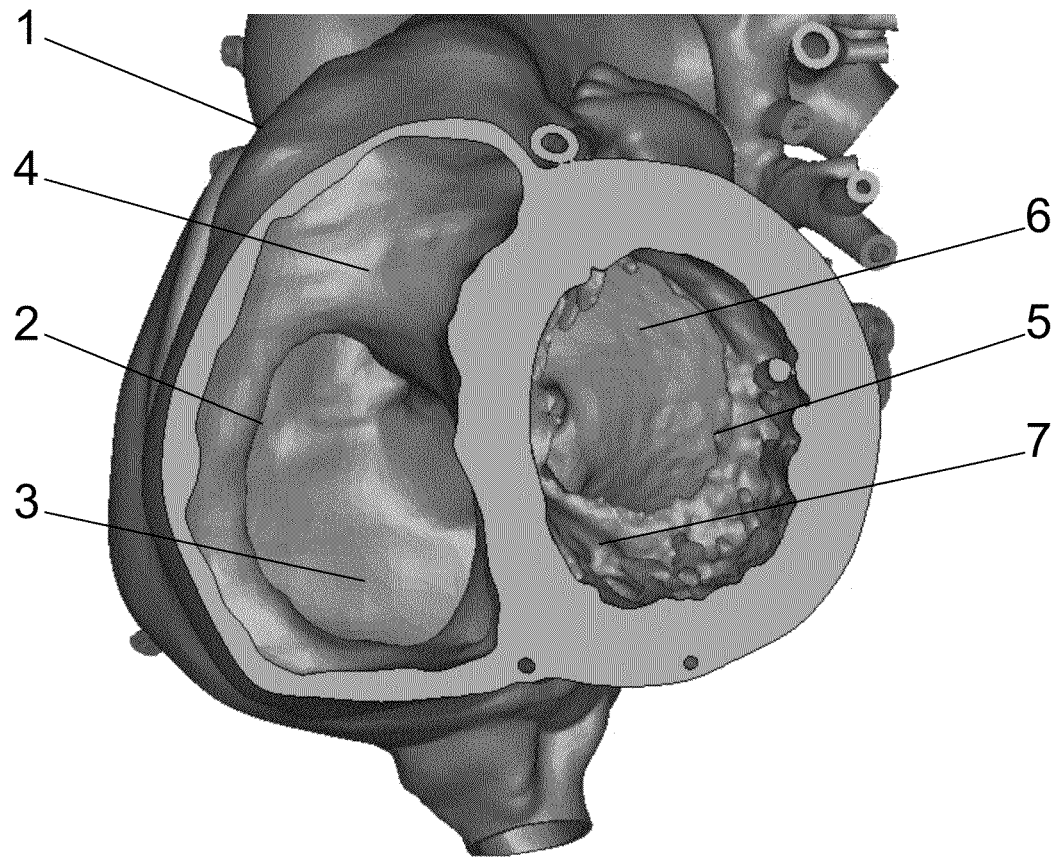
FIG. 1—Illustration of the anatomy of the tricuspid and mitral valve orifices of the heart
FIG. 2—Illustration of a foldable heart valve implant
FIG. 3—Illustration of a plane in which measurements of variations over time could be performed.

1—heart anatomy; 2—Tricuspid valve orifice; 3—right atrium; 4—right ventricle; 5—Mitral valve orifice; 6—left atrium; 7—left ventricle; 8—heart valve; 9—atrial side; 10—ventricular side; 11—heart valve zones showing little movement; 12—intraluminal implant as illustrated by e.g. a heart valve docking structure; 13—channel structure spanning the patient's heart valve onto which functional elements can be attached; 14—cutting plane; 15—cross section of tricuspid valve orifice; 16—oblique cut through left ventricle; 17—maximum distance within the intersection of the orifice; 18—length of intersection curve; 19—best fitting ellipse; 20—best fitting circle; 21—; surface area; 22 outer surface of the intraluminal docking structure; 23 inner surface of the intraluminal docking structure.

DETAILED DESCRIPTION

The application describes particular embodiments but the inventive concept described herein is not limited thereto. Any reference signs in the claims shall not be construed as limiting the scope thereof.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" when referring to recited members, elements or method steps also include embodiments which "consist of" said recited members, elements or method steps.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

The recitation of numerical ranges by endpoints includes all numbers and fractions subsumed within the respective ranges, as well as the recited endpoints.

All documents cited in the present specification are hereby incorporated by reference in their entirety.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention. The terms or definitions used herein are provided solely to aid in the understanding of the invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the enclosed claims, any of the claimed embodiments can be used in any combination.

Provided herein are methods for generating a patient-specific intraluminal implants or endoprosthesis. The term "endoprosthesis" or implant refers to a prosthetic device placed within the body. The term "intraluminal" refers to the fact that they are made to be placed inside a lumen in the human or animal body. A "lumen" refers to any cavity or passageway within the body, and particularly refers to the inside space of a hollow structure. This can be an existing lumen or a lumen created by surgical intervention. This includes lumens such as blood vessels, parts of the gastrointestinal tract, ducts such as bile ducts, parts of the respiratory system, etc. Different types of implants are envisaged, such as but not limited to catheters, stents, grafts, stent-grafts, vena cava filters, tubular expandable frameworks, heart valve frames, or docking structures. It will be understood to the skilled person that in the context of intraluminal implants, most often the implant will ensure/allow a flow of fluid therethrough. However, embodiments wherein the implant blocks the flow of fluid through the lumen are also envisaged.

In particular embodiments, the intraluminal implant envisaged herein is an intraluminal docking structure, which can be used to attach or dock particular functional elements to it. The functional elements envisaged in the context of the docking structures described herein include but are not limited to elements or devices such as stents, grafts, stent-grafts, vena cava filters, tubular expandable frameworks, heart valve frames, etc.

Typically the therapeutic objective of these elements or devices includes restoring or enhancing flow of fluids through the lumen. However, the objective may alternatively be the prevention of flow of fluid or other material through a particular lumen. The functional elements envisaged for use with the docking structures described herein may be standard devices or patient-specific devices.

The methods described herein are envisaged to ensure that the intraluminal implant will be positioned in the optimal location in the patient's lumen. Optimal in this context specifically refers to a location which is known to be stable in motion over time. To this end, the intraluminal implants are provided which are designed to be positioned within specifically selected regions of the lumen wall. In particular embodiments, the implants will be provided with an outer surface which is configured to comprise patient-specific anatomy engagement surfaces or contact points corresponding to these identified anatomical regions of the lumen wall. This ensures that the implant can be nested and remains nested stably against the lumen wall of the patient.

Thus, methods are provided for generating an intraluminal implant specifically fitting a patient's lumen anatomy. Custom-made implants reduce the risk of suboptimal intervention results compared to standard devices. This is specifically applicable to intraluminal devices, especially when the lumen anatomy has a high rate of curvature and/or a non-uniform diameter, as is the case with coronary arteries, cerebral vessels, intestines, etc.

The methods envisaged herein further involve, prior to the manufacture of the intraluminal implant, the selection of parts of the lumen anatomy showing a great stability, such that the intraluminal implant can be designed to fit specifically in these areas of the lumen anatomy.

In particular embodiments, methods are provided for generating a patient-specific intraluminal implant for placement in a lumen, comprising the steps of:
a) identifying for said patient, the anatomical regions in said anatomical area showing greater stability in time based on information from said patient regarding the variation of the anatomy of said lumen in the anatomical area of interest for placing said intraluminal implant, in function of time;
b) identifying and selecting the locations in the regions identified in step (a) which are suitable for use as a base for the contact surface of an intraluminal implant, and
c) generating a patient-specific intraluminal implant based on the information obtained in steps (a) and (b), said implant comprising an outer surface configured to comprise one or more patient-specific anatomy engagement surfaces or contact points corresponding to anatomical regions of the lumen wall identified in step (b) above. The methods envisaged herein may also comprise the step of obtaining information from the patient regarding the variation of the anatomy of the lumen in function of time, more particularly in the anatomical area which is of interest for placing the intraluminal implant.

The location of placement of the implant within the lumen will to some extent be determined by the function of the implant which is to be placed. However, typically the exact position is not critical, such that different positions within one area are possible. Additionally or alternatively, while the structure of the implant can extend over a larger region of the intraluminal wall, interaction/complementarity with only a limited region of the intraluminal wall within this larger region may be sufficient to ensure a stable fit within the lumen. Thus, the methods described herein involve determining, within the "region of interest", i.e. the region which could be used to ensure close interaction of the implant with the intraluminal wall, those regions which are optimal. As detailed above, such optimal regions are typically regions which are characterized by limited movement.

Typically this assessment of variation is an assessment of the variation in function of time. By comparing the movement of different regions in the one or more areas of interest over time, the region with the least movement over time can be identified.

The assessment of movement of a region of the inner wall of a vessel or other lumen can be ensured in different ways, using different parameters. Examples of such parameters include:
  2-dimensional parameters such as but not limited to change in planar circumference of the lumen, area of the lumen, best fit ellipse ellipticity of the lumen, best fit circle diameter of the lumen and/or maximum distance across the lumen;
  3-dimensional parameters such as shortest distance around said lumen, best fit ellipsoid ellipticity of the lumen, short or long axis length of the lumen, best fit cylinder diameter of the lumen, and/or best fit sphere diameter of the lumen; and/or;

Additionally or alternatively, the assessment of movement of a given area can be performed by monitoring the degree of variation or displacement of a point or a surface of the lumen. In particular, the degree of variation or displacement of a point or surface of the lumen can be determined by measurement of the average relative displacement of a specifying anatomical point of the lumen in time. When comparing this to the overall average displacement in time, an anatomical area showing a greater stability can be regarded as an anatomical area or point which is less than 50% of the overall average displacement in time. Alternatively, an anatomical area showing a greater stability can be regarded as an anatomical area or point which shows an average displacement in time of 2 mm or less.

The methods described above allow the identification of the regions, within the anatomical regions of interest, which have the greater stability over time. However, other factors may play a role in the selection of the region of the luminal wall to place the intraluminal implant so as to ensure a stable fit. More particularly, the presence in the vessel wall of anatomical features which allow a closer interaction between the intraluminal implant and the vessel wall may be of interest. These features are typically irregularities in the vessel wall (formed by connective or muscle tissue).

The methods envisaged herein may thus further comprise the step of identifying, within the regions identified to be more stable, those locations which are most suitable for use as a base for the contact surface of an intraluminal implant.

The methods described herein further comprise generating an implant having specific features based on this information.

In particular embodiments, the intraluminal implant envisaged is an intraluminal docking structures, in these embodiments, the methods will comprise generating a device which comprises, in addition to the outer surface described above, an inner surface comprising one or more docking features for detachably engaging said inner surface of said intraluminal docking structure with said functional element.

The general structure of the intraluminal docking structure may be standard, but is typically also based on patient information regarding the anatomy of the patient's lumen and the functional element to be introduced into the lumen.

The intraluminal docking structures envisaged in the context of the present application may thus have different shapes and sizes. The general features of such docking structures are known in the art. In some embodiments they are to some extent hollow to allow introduction of a functional element therein. In particular embodiments, the intraluminal docking structures are envisaged to comprise a body forming a channel structure spanning part the patient's lumen. Thus, intraluminal docking structures are typically characterized by an outer surface, at least part of which is envisaged to contact the luminal wall and an inner surface, at least part of which will contact the functional element.

Generally, the intraluminal implant is defined by its envisaged function, its envisaged position in the lumen and the natural flow of blood or other fluids through the device. More particularly, the distal end of the implant is the end at which the blood flow exits the intraluminal implant and the proximal end is the end at which the blood flow enters the intraluminal implant. This is of particular interest where the intraluminal implant comprises a body extending in the direction of the lumen and different contact areas with the lumen wall are envisaged.

In particular embodiments the intraluminal implant is envisaged to comprise one or more toroidal attachment structures for positioning/attachment in the lumen. More particularly, intraluminal implants are envisaged which comprise two toroidal attachment structures connected by a central body. The term "toroidal" as used herein typically refers to a torus or ring shaped structure.

As detailed above, the methods disclosed herein generally rely on information relating to the patient's lumen anatomy. This type of information is typically obtained through known medical imaging techniques. The term "medical imaging" as used herein refers to techniques and processes used to create images of the human or animal body (or parts and function thereof), typically for clinical purposes (medical procedures seeking to reveal, diagnose or examine disease) or medical science (including the study of normal anatomy and physiology).

The information relating to the variation of the lumen anatomy in function of time for use in the methods described herein is obtained from a patient by three dimensional (3D) imaging of the lumen in function of time. The imaging information can be obtained using any type of imaging apparatus or imaging technique which allows imaging or scanning the patient's lumen in function of time in an accurate manner. These may include equipment such as cameras and scanners for industrial, household or medical use. In particular embodiments the imaging techniques and appliances used are typical medical imaging tools such as, but not limited to computer tomography (CT) scans including for instance multi-slice CT (MSCT) scans, magnetic resonance imaging (MRI) scans, ultrasound, 3D ultrasound, Positron emission tomography (PET) scans, Single-photon emission computed tomography (SPECT) scans or other imaging modalities. A summary of medical imaging has been described in "Fundamentals of Medical imaging", by P. Suetens, Cambridge University Press, 2002.

The methods described herein comprise the step of generating a patient-specific intraluminal implant, which is characterized by specific features which will determine the position of the intraluminal implant in the patient and which are based on the selection of the regions in the intraluminal wall suitable for the placement or anchoring of the implant. More particularly, the outer surface of the intraluminal implant, i.e. the surface contacting the intraluminal wall, is provided with one or more patient-specific anatomy engagement surfaces or patient-specific contact points.

More particularly, as used herein the terms "patient-specific anatomy engagement surfaces" or "patient-specific contact points" relate to surfaces which are designed based on an individual patient's lumen anatomy, thereby including features which have a custom fit on a specific location in a specific patient's lumen anatomy. The use of the patient-specific surface in the structures as disclosed herein allows to ensure an improved or optimized accuracy of the positioning of the implant. Where the implant is an intraluminal docking station, this further increases accuracy of the positioning of the functional element.

In particular embodiments the implant structures as disclosed herein comprise at least two discrete patient-specific elements or surfaces which ensure a patient-specific fit on the anatomy of a patient. In particular embodiments, the patient-specific surface conforms to or is complementary with at least part of the patient's anatomy. More particularly, as regions are selected which comprise anatomical features of interest, the patient-specific surfaces are designed to ensure a close fit with the anatomical features of interest.

As a result the devices envisaged herein can be made to have a rigid structure (or expand/deploy into a rigid structure) while ensuring a perfect fit in the lumen of the patient. Indeed, the structure need not adjust to the patient's anatomy upon placement, as it is designed to securely fit the patient's anatomy. Moreover as the devices envisaged herein are configured by way of the patient-specific surface(s) to ensure a perfect with in one specific position within the patient, they do not require identifying the optimal fit during placement.

The patient-specific surfaces are provided on the outer surface of the intraluminal implant, more particularly, those parts of the outer surface envisaged to be in direct contact with the luminal surface. In particular embodiments, where the implant comprises one or more toroidal attachment structures, the patient-specific surfaces are provided on the outer surface of the one or more toroidal attachment structures.

Where the intraluminal implant is a docking structure, the methods envisaged herein further comprise providing the intraluminal docking structure with one or more docking features for detachably engaging a functional element. Typically, the docking features are provided on the internal surface of the intraluminal docking structure. The nature of the docking features will be determined by the nature of the functional element for which the docking structure is intended. In a particular embodiment according to the method disclosed herein, said docking features include anchoring components engaging said functional element by friction, barb, clip, staple, post, eyelet or hook. In particular the docking features anchor to the functional element through friction. This friction can be increased by making the edges rough in nature (texturing) or in a more rigid material. In particular embodiments the docking features of the intraluminal docking structure comprise roughened surfaces while no roughened surfaces for docking purposes are present on the functional element. More particularly, where the functional element is a standard element such as a standard TAVI device, the functional element is not roughened. However, other embodiments are also envisaged. In particular embodiments the functional element comprises roughened surfaces while no roughened surfaces for docking purposes are present on the docking features of the intraluminal docking structure. In particular embodiments both the docking features of the intraluminal docking structure and the functional element comprise roughened surfaces.

In particular embodiments, the intraluminal docking structure disclosed herein is envisaged for use with a functional element which is selected from a valve, plug, mesh or a component for eluting a drug. Indeed, docking stations are of particular interest to allow the replacement of a functional element while maintaining the docking in the lumen. In particular embodiments, the intraluminal docking structure is a temporary structure used for placement of an endoprosthesis or a drug eluting component. More commonly however, the intraluminal docking structure in combination with a functional element such as a valve or stent forms an endoprosthesis envisaged to be maintained within the body.

As detailed above, the general structure of the implant will be determined by the nature of the function (or functional element) for which it is intended and the anatomy of the lumen where it is to be placed. The length and diameter of the intraluminal implant thus, in part, depends on the anatomy of the lumen into which it is to be deployed and its intended function. For example, coronary stents typically have a length between 10 and 30 mm and a diameter (when deployed) between 2 and 5 mm, whereas a thoracic endoprosthesis typically has a length between 10 and 20 cm and a diameter between 25 and 40 mm.

In particular embodiments the intraluminal implants envisaged are at least partially covered by a graft material such as but not limited to an engineered, animal, human or tissue. In further particular embodiments, the endoprosthesis is a heart valve and comprises an engineered heart valve (i.e. of human or animal material) integrated into the structure. In particular embodiments, the implant is a docking structure which itself is envisaged to be at least partially covered by graft material or which is envisaged for use with a functional element which is at least partially covered by graft material.

In certain embodiments, the intraluminal implant as disclosed herein is an endovascular implant. In further particular embodiments the intraluminal implant is a heart valve. In further embodiments, the intraluminal implant is a docking structure, such as a heart valve docking structure. This latter embodiment will be described more in detail below.

In a particular embodiment the intraluminal implant can be used to deliver drugs or medicine, either directly or by way of a functional element. Upon introduction, the intraluminal implant and/or where applicable the functional element are prone to calcification. To prevent or minimize the calcification several treatments have been employed before the tissue is fixed. Some strategies include treating the implanted structures with ethanol, metallic salts, detergents, biophosphonates, coimplants of polymeric controlled release drug delivery systems, and covalent attachment of anticalcifying agents. In the particular embodiment the implanted structure is treated in 40% to 80% ethanol for 20 to 200 hours before fixation in a buffered glutaraldehyde solution. The ethanol pretreatment prevents calcification in of the structure after implantation and serves to remove cholesterol and phospholipids from the tissue before fixation.

In particular embodiments, the methods as disclosed herein further provide that the implant or part thereof is transitionable from a collapsed state to an expanded state. The intraluminal implant as envisaged herein may be self-expanding or balloon expandable. A self-expanding structure has the ability to revert readily from a reduced profile configuration to a larger profile configuration in the absence of a restraint upon the device that maintains the device in the reduced profile configuration. Balloon expandable refers to a device that comprises a reduced profile configuration and an expanded profile configuration, and undergoes a transition from the reduced configuration to the expanded configuration via the outward radial force of a balloon expanded by any suitable inflation medium. The implant is particularly capable of collapsing to a diameter small enough to pass through the desired introducer size.

More particularly, the intraluminal implant is transitionable from a collapsed state to an expanded state where the equilibrium shape of the structure can be the expanded state, the collapsed state or a state in between. More particularly, the intraluminal implant comprises two equilibrium stages. The transition from one state to another may be triggered through an activation mechanism bringing the structure from one state to the other and/or blocking the implant in a specific state. Accordingly, these structures are transported in a collapsed state towards the anatomical position where it is eventually deployed. These types of expandable structures require the use of shape memory alloys such as Nitinol. If the location or performance of the intraluminal implant is not acceptable, the support structure may be caused to contract by changing its temperature, causing it to return to its preset "remembered" shape, which in this case is a smaller, radially collapsed shape. The temperature controlling media could be a fluid such as saline, and could be delivered while a catheter is inserted through the support structure. This would cause the intraluminal implant to collapse down on the catheter allowing removal or possibly redeployment. Other shape memory materials are available, and may have more desirable mechanical properties for use as expandable intraluminal implant.

In another particular embodiment, the intraluminal implant is transitionable from a collapsed state to an expanded state through an activation mechanism bringing the structure into the expanded state. The activation mechanism may be a mechanical switch or a blocking element. Preferably, this type of intraluminal implant is a balloon expandable intraluminal implant where typically biocompatible alloys, such as stainless steel, cobalt-chromium, or other materials known in the art are used. The balloon expandable intraluminal implant is deployed in any way desired, using the typically known methods available in the prior art. If the location or performance of the intraluminal implant is not acceptable, the support structure may be caused to contract by deflating the balloon causing it to return to its collapsed state, allowing removal or possible redeployment.

In a particular embodiment, the intraluminal implant is a docking structure and a combination of the intraluminal docking station and functional element is provided as a self-expanding endoprosthesis. In more particular embodiments, the implant such as the docking structure is a recapturable self-expanding device. Typically such recapturable devices are braided from a superelastic or high strength alloy and have relatively low radial strength. As they are pulled back into a sheath they collapse on their diameter and lengthen facilitating recapturability. Not all braided self-expanding structures are recapturable.

In a further particular embodiment, it is provided that said intraluminal implant or part thereof is adapted to retract radially in the collapsed state and extend radially in the expanded state.

In particular embodiments of the method disclosed herein said intraluminal implants, such as but not limited to intraluminal docking structures and optionally the functional element envisaged for use therewith are manufactured by additive manufacturing. In more particular embodiments, said implant, such as a docking structure and/or the functional element for use therewith, is manufactured as a single part.

Additive Manufacturing can be defined as a group of techniques used to fabricate a tangible object typically using 3D computer aided design (CAD) data. Currently, a multitude of Additive Manufacturing techniques is available, including Selective Laser Sintering, stereolithography, Fused Deposition Modeling, foil-based techniques, etc. Selective laser sintering (SLS) and selective laser melting use a high power laser or another focused heat source to sinter or weld small particles of plastic, metal, or ceramic powders into a mass representing the 3D object to be formed. Fused deposition modeling and related techniques make use of a temporary transition from a solid material to a liquid state, usually due to heating. The material is driven through an extrusion nozzle in a controlled way and deposited in the required place as described among others in U.S. Pat. No. 5,141,680. Foil-based techniques fix coats to one another by means of gluing or photo polymerization or other techniques and cut the object from these coats or polymerize the object. Such a technique is described in U.S. Pat. No. 5,192,539.

Typically AM techniques start from a digital representation of the 3D object to be formed. Generally, the digital representation is sliced into a series of cross-sectional layers which can be overlaid to form the object as a whole. The AM apparatus uses this data for building the object on a layer-by-layer basis. The cross-sectional data representing the layer data of the 3D object may be generated using a computer system and computer aided design and manufacturing (CAD/CAM) software.

The material used to manufacture the disclosed structures may depend on the (additive) manufacturing method used and the specifications of the endoprosthesis to be manufactured. In particular embodiments, the intraluminal implant is made of a material which is biocompatible as well as compatible with additive manufacturing, including shape memory alloy, super elastic alloy, polymer, stainless steel or any other material which is used in endovascular prostheses. Preferably said material is a shape memory and/or super elastic material, including metals, metal alloys and polymers. In particular embodiments, the wires used for making the endoprosthesis comprise nitinol, stainless steel, titanium, platinum, pyrolitic carbon, polyglycolic acid, expanded polytetrafluoroethylene, polyethylene terephtalate, polylactic acid or any other (biocompatible) metal, ceramic or polymer known in the art.

In particular embodiments, the intraluminal implant may further be coated. In further embodiments, the coating is an (inert) coating selected from the group consisting of polysulfone, silicone rubber, polyurethane, synthetic glycocalix, amorphous silicon carbide, diamond-like carbon, magnesium phosphate, magnesium oxide, or mixtures thereof.

In particular embodiments, the intraluminal implants envisaged herein comprise a flexible biocompatible contractible fabric or an auxetic material. The contractible aspect of the intraluminal implant is the result of the structure and/or material of the intraluminal implant. When the structure is provided with mechanical hinges that allow folding of the structure the ratio of the amount of material versus free space should be low to allow the contraction. Alternatively, elastic materials may also be used to provide the collapsible characteristics, whereby regions in the structure having a higher elasticity act as bending points. Typical flexible biocompatible materials include, but are not limited to, polymers, such as epoxies, acrylates, polycarbonate, polyolefins, polyamide, PEEK, polyurethanes, Poly(Acrylonitrile, Butadiene, Styrene) (ABS), sulphones and/or Polyethylenimine; metals, such as stainless steel, aluminum, cobalt, chrome, gold, platinum, nickel or alloys thereof; and/or ceramics, such as aluminae, Zroxide and/or Si carbide.

In a particular embodiment said intraluminal implant is made of a bio-absorbable material.

The patient envisaged in which the intraluminal implants described herein can be used may be a human or animal patient. Particularly, said intraluminal implant can be an intraluminal docking structure such as a heart valve docking structure.

More particularly, methods are provided wherein said patient-specific intraluminal implant is a heart valve comprising a distal toroidal attachment structure a proximal toroidal attachment structure; and a body structure linking the distal toroidal attachment structure to the proximal toroidal attachment structure, thereby spanning the patient's heart valve. In particular embodiments, these methods comprise identifying for said patient, the anatomical regions in the anatomical area of said heart valve showing greater stability in time; identifying and selecting the locations in the regions identified, which are suitable for use as a base for the contact surface of a heart valve, and generating a patient-specific heart valve based on the information obtained in the previous identification steps such that said distal toroidal attachment structure comprises patient-specific anatomy engagement surfaces or contact points corresponding to anatomical regions on the outflow side of the patient's heart valve anatomy and said proximal toroidal attachment structure comprises patient-specific anatomy engagement surfaces or contact points corresponding to anatomical regions on the inflow side of the patient's heart valve anatomy. In particular embodiments, the patient-specific intraluminal implant can be a heart valve docking structure and the heart valve docking structure comprises a distal toroidal attachment structure, a proximal toroidal attachment structure, and a body structure linking the distal toroidal attachment structure to the proximal toroidal attachment structure, thereby spanning the patient's heart valve such as described above.

The application further provides intraluminal implants such as those obtainable by the methods described herein. More particularly, the application provides intraluminal implants which comprise a body structure spanning a specific patient's lumen with an outer surface configured to comprise one or more patient-specific anatomy engagement surfaces or contact points corresponding to patient-specific anatomical regions of the lumen wall, wherein said patient-specific anatomical regions of the lumen wall are pre-operatively identified anatomical regions showing greater stability in time.

In particular embodiments, the outer surface of the intraluminal implants envisaged herein comprise an outer surface comprising both patient-specific anatomy engagement surfaces or contact points and non-patient-specific surfaces, wherein the non-patient specific surfaces correspond to anatomical regions of the lumen wall are pre-operatively identified anatomical regions showing lesser stability in time. Thus, in particular embodiments the patient-specific anatomy engagement surfaces or contact points do not extend over the entire outer surface of the implant, but represent one or more discrete areas on the outer surface of the implant. In particular embodiments, the patient-specific anatomy engagement surfaces or contact points are characterized by an irregular freeform surface, while the non-patient-specific surface parts are characterized by a regular and/or smooth surface. In particular embodiments, the outer surface of the implant comprises a combination of patient-specific surface areas and toroidal attachment structures. In particular embodiments, a toroidal attachment structure can be positioned within a patient-specific surface area. In further embodiments, the patient-specific anatomy engagement surface is present on the one or more toroidal attachment structures.

Thus in particular embodiments, intraluminal implants are provided which comprise a structure characterized by a central hollow body which connects:
  a distal toroidal attachment structure combined with one or more patient-specific anatomy engagement surfaces or contact points corresponding to anatomical regions on the outflow side of the patient's heart valve anatomy; and
  a proximal toroidal attachment structure combined with one or more patient-specific anatomy engagement surfaces or contact points corresponding to anatomical regions on the inflow side of the patient's heart valve anatomy;

In particular embodiments, the application provides intraluminal docking structures comprising a body structure spanning a specific patient's lumen, an outer surface configured to comprise one or more patient-specific anatomy engagement surfaces or contact points corresponding to patient-specific anatomical regions of the lumen wall; and an inner surface comprising one or more docking features for detachably engaging said inner surface of said intraluminal docking structure with a functional element; wherein said patient-specific anatomical regions of the lumen wall are pre-operatively identified anatomical regions showing greater stability in time.

In particular embodiments, heart valve docking structures are provided which comprise a structure characterized by a central hollow body which connects:

- a distal toroidal attachment structure comprising patient-specific anatomy engagement surfaces or contact points corresponding to anatomical regions on the outflow side of the patient's heart valve anatomy; and
- a proximal toroidal attachment structure comprising patient-specific anatomy engagement surfaces or contact points corresponding to anatomical regions on the inflow side of the patient's heart valve anatomy;

More particularly, the heart valve docking structures are characterized in that the patient-specific engagement surfaces or contact points correspond to anatomical regions of the intraluminal wall neighboring said valve characterized by greatest stability in time.

More particularly, the distal and proximal toroidal attachment structures of the heart valve docking station are constructed and configured to be positioned, when in use, against an annulus defined by tissue surrounding the patient's tricuspid, mitral, aortic or pulmonary valve, and in particular the patient's tricuspid or mitral valve. More particularly, the heart valve docking structure is particularly suitable for use onto the patient's tricuspid or mitral valve. As these heart valves are difficult to reach using the currently available minimally invasive valve devices, the heart valve docking structure as disclosed herein would be particularly suitable for the tricuspid or mitral heart valves. The application further provides combinations of intraluminal docking structures as described herein and functional elements for use therewith.

The application further provides methods for introducing a functional element into the lumen of a patient, using the intraluminal docking structures described herein. More particularly these methods involve positioning the intraluminal docking structure specifically and correctly into the patient's anatomy. The intraluminal docking structures as disclosed herein are introduced into the patient using a guide wire.

This will be exemplified herein for the positioning of a heart valve docking structure. While the traditional way to repair or replace a heart valve is to perform a sternotomy, the intraluminal docking structures disclosed herein can be deployed without requiring invasive surgery. In particular embodiments, the methods for introducing the docking structures involve the following steps:

- creating an incision in such location as traditionally required for a transcatheter heart valve access, for instance including but not limited to: femoral veins or arteries, transapical, transaortic or subclavian access, transjugular, transcarotid;
- introduction of a sheath and guide wire
- optionally, performing of a balloon valvuloplasty (breaking open of the diseased valve by inflating a balloon in it)
- collapsing of the docking and provision onto the catheter. It will be brought over the guide wire to the location of deployment.
- Deployment of the docking structure. The deployment can be as a self-expanding device by pushing it out of the catheter and by the device restoring to its original state because of elasticity. Alternatively a mechanical deformation mechanism (balloon, pulling, pushing, . . . ) and a locking mechanism can be used that allows for opening and locking the deployment degree of freedom.
- once in place the functional element is released from its delivery system and onto the docking station. The functional element can be deployed using a transcatheter approach.

The present invention will be illustrated by the following non-limiting embodiments.

EXAMPLES

Identification of Suitable Locations for Use in the Development of a Patient-Specific Intraluminal Implant The present example provides a particular embodiment which may be used to identifying and selecting the locations in a patient's anatomy that are suitable for use as a base for the patient-specific contact surfaces of a intraluminal implant, such as but not limited to, an intraluminal docking structure.

Figure 2:
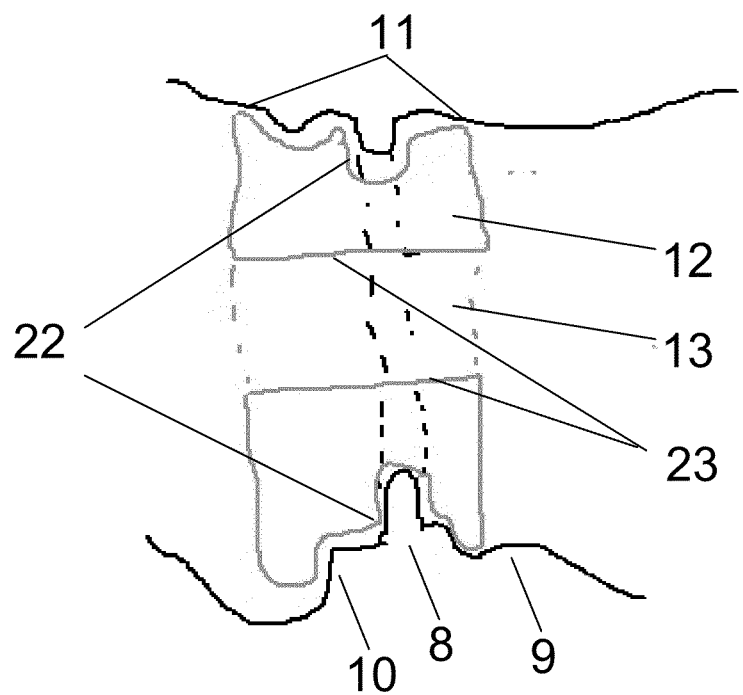
Figure 3:
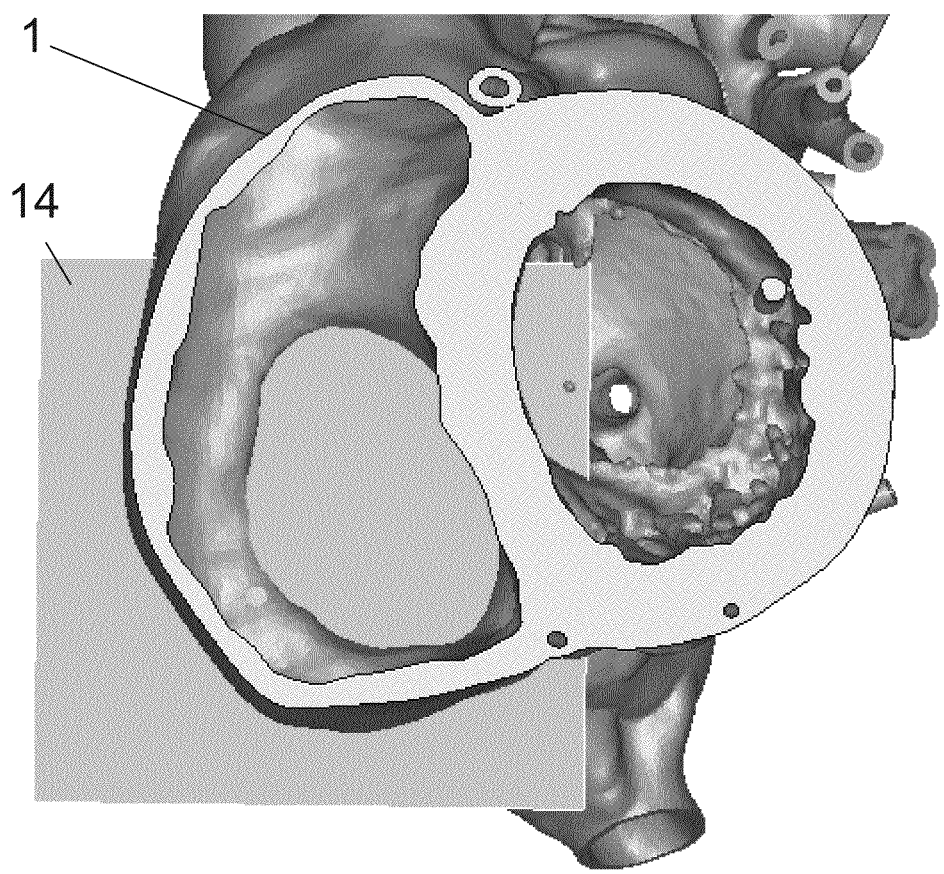
Figure 4:
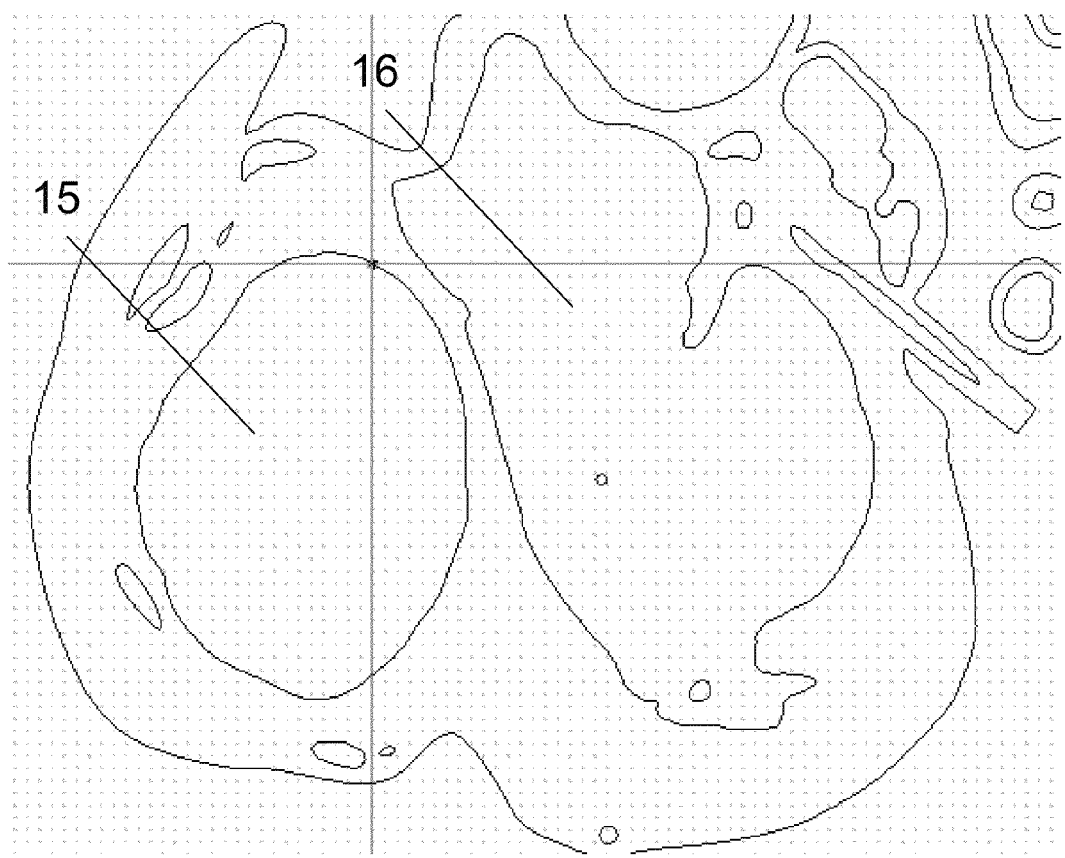
FIG. 4—The cross section as cut with the plane of FIG. 3
FIG. 5A-5E—Illustration of the measurement of the (A) maximum distance within the intersection of the orifice; (B) length of intersection curve; (C) best fitting ellipse, long and short axis length or ellipticity (long/short axis length); (D) best fitting circle, smallest fitting or maximum fitting diameter; (E) surface area.
Figure 5:
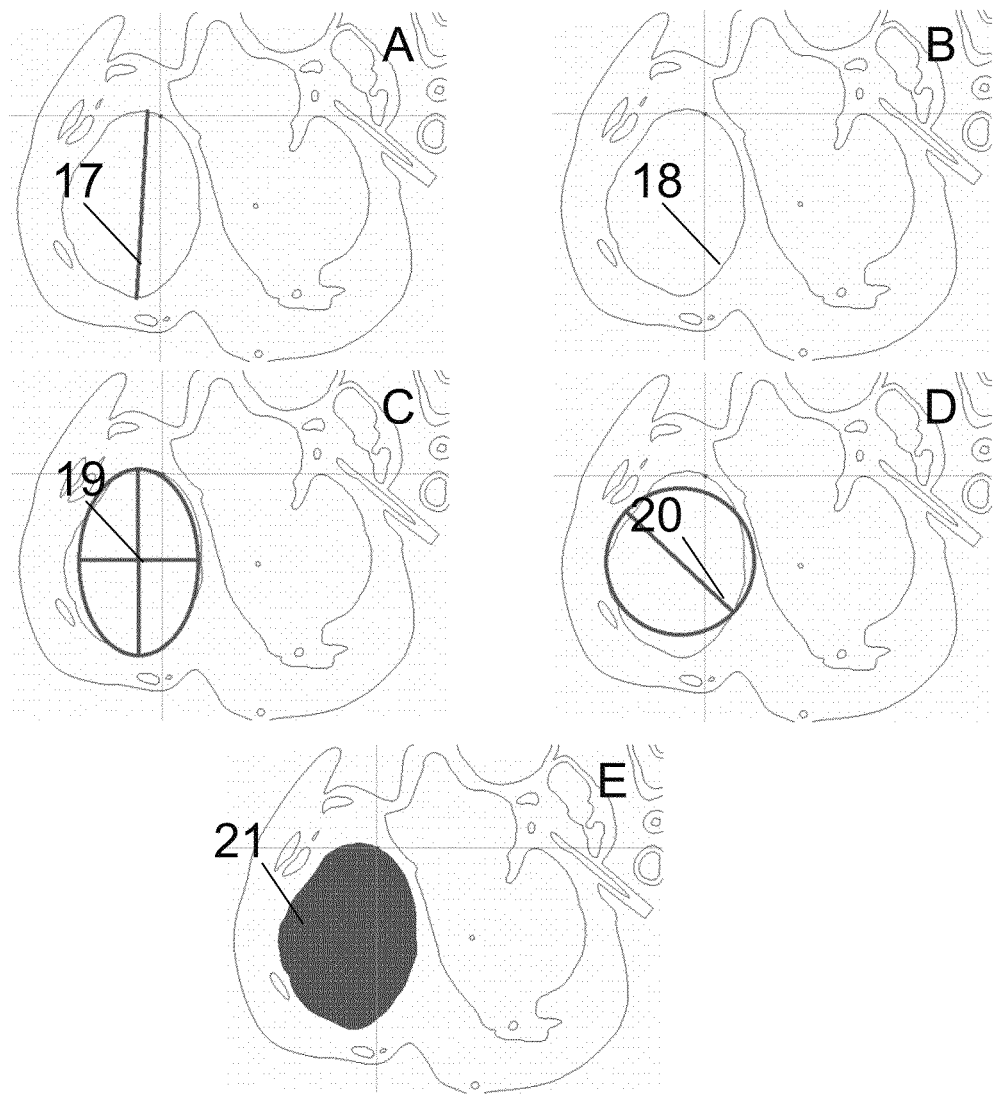
Figure 6:
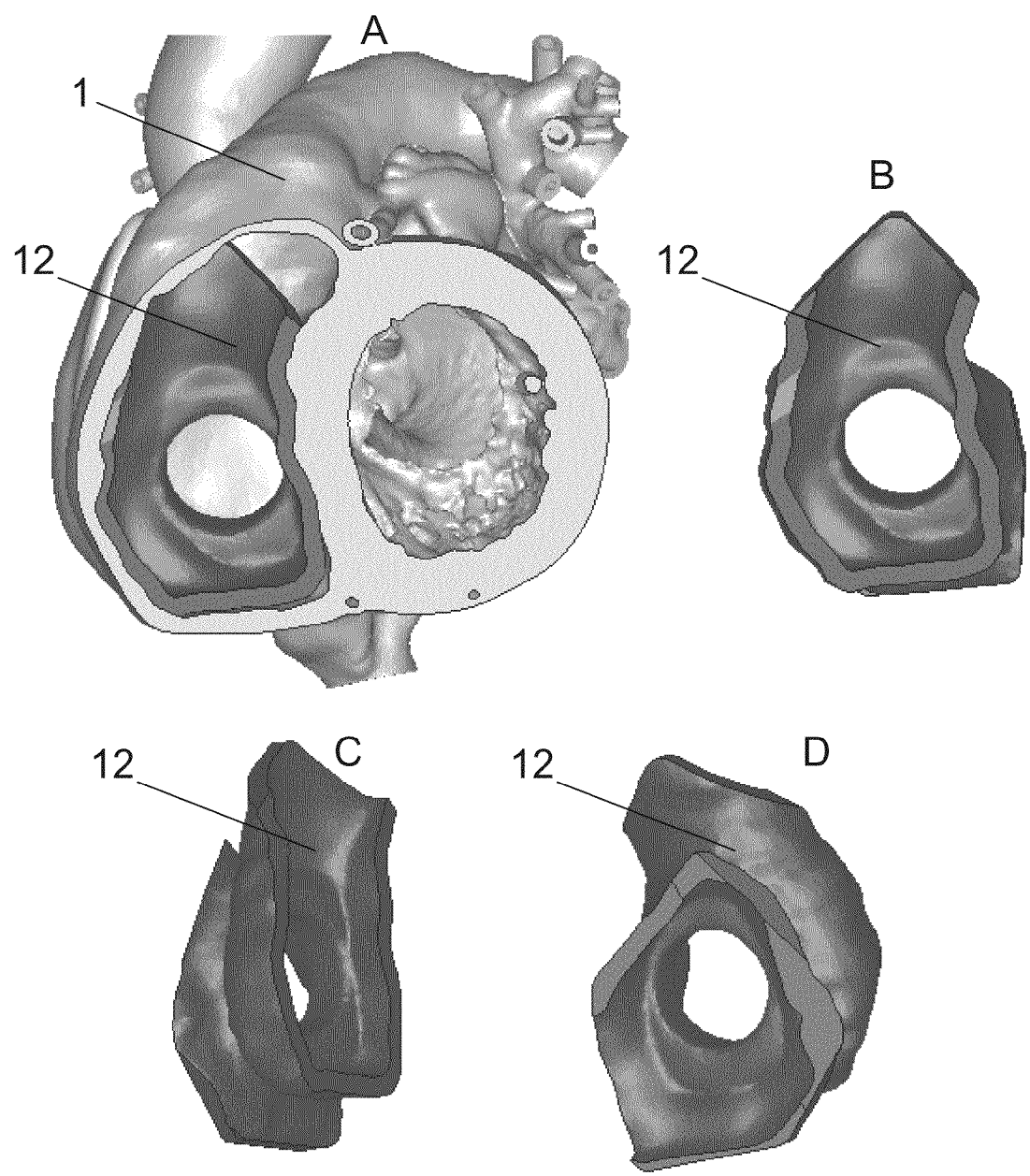
FIG. 6A-6D—Example of the resulting docking structure (B-D) and its position in the tricuspid valve (A)

In first instance the patient's anatomy onto which the intraluminal docking structure needs to be deployed is identified (e.g. the tricuspid valve a shown in FIG. 1). Using medical imaging equipment the variation of the anatomy of tricuspid valve is monitored in function of time. For this purpose a plane is identified in which the measurements are performed (FIG. 3), thereby providing cross section images (FIG. 4) of the plane cut in function of time. From these images specific parameters are measured such as for instance the maximum distance within the intersection of the tricuspid valve orifice (FIG. 5A); the length of intersection curve (FIG. 5B); the best fitting ellipse (FIG. 5C); the best fitting circle (FIG. 5D); and/or the surface area (FIG. 5E). These data serve as a basis for identifying for said patient, the anatomical regions in said anatomical area showing greater stability in time and identifying and selecting the locations which are suitable for use as a base for the contact surface of an intraluminal implant. On the basis of this information a patient-specific intraluminal implant is generated (FIG. 6). The positioning of an exemplary implant in a lumen is illustrated in FIG. 2. The implant (12) is characterized by an outer surface (22) comprising one or more patient-specific anatomy engagement surfaces or contact points corresponding to locations of the anatomical regions of the lumen wall which have been selected according to the methods described herein.

In further embodiments, where the intraluminal implant is a docking structure, it may further comprise an inner surface (23) comprising one or more docking features for detachably engaging the inner surface of with a functional element.

The invention claimed is:

1. A method for generating a patient-specific intraluminal implant, comprising the steps of:
    a) identifying for a patient, based on information regarding variation in function of time of the anatomy of said lumen in an anatomical area of interest for placing said intraluminal implant, anatomical regions in said anatomical area showing greater stability in time;
    b) identifying and selecting locations in the anatomical regions identified in step (a) which are suitable for use as a base for the contact surface of a intraluminal implant, and
    c) generating a patient-specific intraluminal implant based on the information obtained in steps (a)-(b), wherein the generated patient-specific intraluminal implant comprises an outer surface having one or more patient-specific anatomy engagement surfaces or contact points corresponding to the locations of the anatomical regions of the lumen wall identified and selected in step (b).

2. The method according to claim 1, wherein said step of identifying anatomical regions showing greater stability in time comprises performing an assessment, wherein the assessment is based at least in part on one or more of:
    2-dimensional parameters comprising change in planar circumference, area, best fit ellipse ellipticity, best fit circle diameter and/or maximum distance across a lumen;

3-dimensional parameters comprising shortest distance around said lumen, best fit ellipsoid ellipticity, short or long axis length, best fit cylinder diameter, and/or best fit sphere diameter; and/or;

the degree of variation or displacement of a point or surface.

3. The method according to claim 1, wherein said patient-specific intraluminal implant is an intraluminal docking structure for a functional element, and wherein the patient-specific intraluminal implant further comprises:

an inner surface comprising one or more docking features for detachably engaging said inner surface of said intraluminal docking structure with said functional element.

4. The method according to claim 3, wherein said functional element is one of a valve, plug, mesh or drug eluting component.

5. The method according to claim 3, wherein said docking features include anchoring components engaging said functional element by friction, barb, clip, staple, post, eyelet or hook.

6. The method according claim 1, wherein the patient-specific anatomy engagement surfaces are located both in regions at a distal end and at a proximal end of said lumen wall.

7. The method according to claim 6, wherein the generated patient-specific intraluminal implant further comprises one or more attachment structures for attachment in said lumen.

8. The method according to claim 1, wherein the generated patient-specific intraluminal implant or part thereof is transitionable from a collapsed state to an expanded state.

9. The method according to claim 8, wherein said generated patient-specific intraluminal implant comprises a distal toroidal attachment structure and a proximal toroidal attachment structure, and wherein each of the distal toroidal attachment structure and the proximal toroidal attachment structure can be independently expanded to approximately it full diameter.

10. The method according to claim 1, wherein said generated patient-specific intraluminal implant or part thereof is adapted to retract radially in the collapsed state and extend radially in the expanded state.

11. The method according to claim 1, wherein said generated patient-specific intraluminal implant further comprises a flexible biocompatible contractible fabric or an auxetic material or structure.

12. The method according to claim 1, wherein generating said patient-specific intraluminal implant further comprises generating the patient-specific intraluminal implant as a single part through additive manufacturing.

13. A method of generating a patient-specific heart valve docking structure for a heart valve of a patient, the method comprising:

(a) identifying for said patient, anatomical regions in an anatomical area of said heart valve showing greater stability in time;

(b) identifying and selecting the locations in the identified anatomical regions suitable for use as a base for at least one contact surface of the heart valve docking structure, and (c) generating the patient-specific heart valve docking structure based on the information obtained in steps (a) and (b), such that wherein the generated patient-specific heart valve docking structure comprises a body structure which links a distal toroidal attachment structure and a proximal toroidal attachment structure, and wherein said distal toroidal attachment structure comprises patient-specific anatomy engagement surfaces or contact points corresponding to anatomical regions identified on the outflow side of the patient's heart valve anatomy, and wherein said proximal toroidal attachment structure comprises patient-specific anatomy engagement surfaces or contact points corresponding to anatomical regions identified on the inflow side of the patient's heart valve anatomy.

* * * * *